United States Patent [19]

Milano

[11] 4,035,396

[45] July 12, 1977

[54] PROCESS FOR PREPARING ALKYLANTHRAQUINONE

[75] Inventor: James Milano, Erial, N.J.

[73] Assignee: E. I. Du Pont de Nemours and Company, Wilmington, Del.

[21] Appl. No.: 666,056

[22] Filed: Mar. 11, 1976

Related U.S. Application Data

[63] Continuation-in-part of Ser. No. 565,852, April 7, 1975, abandoned.

[51] Int. Cl.² .......................................... C07C 49/68
[52] U.S. Cl. ...................................................... 260/369
[58] Field of Search ..................................... 210/369

[56] References Cited

U.S. PATENT DOCUMENTS

| | | | |
|---|---|---|---|
| 1,856,231 | 5/1932 | Stowell | 260/369 |
| 1,890,040 | 12/1932 | Luttringhaus et al. | 260/369 UX |
| 2,842,562 | 7/1958 | Bloom | 260/369 |
| 3,032,560 | 5/1962 | Dawsey | 260/369 |

*Primary Examiner*—Allen B. Curtis
*Attorney, Agent, or Firm*—James A. Costello

[57] ABSTRACT

A solution of alkylbenzoylbenzoic acid in a solvent that resists sulfonation is contacted at or below about 95° C with oleum to effect ring closure. The product alkylanthraquinone is obtained in solution from which the alkylanthraquinone can be isolated.

3 Claims, No Drawings

PROCESS FOR PREPARING ALKYLANTHRAQUINONE

CROSS-REFERENCE TO RELATED APPLICATION

This is a continuation-in-part application of copending U.S. application Ser. No. 565,852, filed on April 7, 1975 now abandoned.

BACKGROUND OF THE INVENTION

This invention concerns a process for preparing alkylanthraquinone. Known processes for preparing alkylanthraquinones include the following:

i. heating alkylbenzoylbenzoic acid in a stoichiometric excess of sulfuric acid or oleum at below 100°C, ii. heating methyl- or ethyl -benzoylbenzoic acid in the presence of catalytic amounts of oleum at temperatures of 100° C to 300° C in the presence of up to 25% of an inert solvent, e.g. trichlorobenzene, based on the weight of the benzoylbenzoic acid.

said processes suffer from several infirmities: type (i) processes are slow and tend toward low yields of alkylanthraquinones whose alky groups contain more than two carbon atoms; type (ii) processes present handling difficulties because of the high temperatures employed, said high temperatures also tending to cause decomposition of the alkylanthraquinones whose alkyl groups contain more than one or two carbon atoms.

Patents which are representative of the state of this art include: U.S. Pat. No. 2,842,562 (catalytic amount of sulfuric acid or oleum); U.S. 3,032,560 (no solvent is present during the reaction); U.S. Pat. No. 1,856,231 (produces a nitroanthraquinone); U.S. 1,890,040 (condensation reaction of a quinone with a 1,3 butadiene hydrocarbon); German Pat. No. 2,058,121 (sulfur trioxide is the cyclization agent); and French 1,528,795 (no solvent is present during the reaction).

SUMMARY OF THE INVENTION

In a process for preparing alkylanthraquinone comprising heating alkylbenzoylbenzoic acid in the presence of oleum, the improvement of this invention comprises i. forming a solution of one part of alkylbenzoylbenzoic acid in at least five parts by weight of an inert solvent, said alkyl group having from 1 to 8 carbon atoms, ii. reacting the solution of (i) with at least four parts of oleum per part of alkylbenzoylbenzoic acid at a temperature up to about 95° C.

By "inert solvent"is meant one that does not take part in the ring closure reaction. Such solvents resist sulfonation under the reaction conditions employed although some sulfonation will usually occur. Useful solvents include but are not limited to trichlorobenzene and dichlorobenzene. from about 7 to 30% of the solvent will usualy sulfonate during the ring closure reaction. Of course, the degree of sulfonation is influenced by agitation, distribution of the solution as it is charged, heating profile, and the like.

The alkyl group on the starting reactant and final product has 1 to 8 carbon atoms, preferably 4 or 5 carbon atoms. Especially preferred alkyl substituents are tertiary butyl and tertiary pentyl (amyl) groups. Commercially available starting reactants are acceptable for use herein. One skilled in the art will appreciate that, depending upon the desired isomeric form of the alkylanthraquinone, a particular isomeric form of the starting alkylbenzoylbenzoic acid would be preferred which is most likely to produce maximum yields of said isomeric alkylanthraquinone.

The oleum employed can be of technical grade or better. Best results are obtained when the sulfur trioxide level does not exceed about 10 to 11% of the oleum by weight. Sulfur trioxide levels above 10 to 11% increase the likelihood of a successful competing sulfonation reaction and will thus give lower product yields. Preferred starting concentrations should contain at least enough sulfur trioxide, about 4 or 5%, to insure an excess of sulfur trioxide throughout the course of the reaction. Preferred levels of sulfur trioxide in sulfuric acid are between 5to 10%, i.e. 5 to 10% oleum.

DETAILS OF THE INVENTION

Alkylbenzoylbenzoic acids (the starting reactants herein) are customarily prepared by the Friedel-Crafts reaction from phthalic anhydride and an alkyl-substituted benzene. The reaction can be performed using an inert solvent and a chemical equivalent of the reactive alkyl-substituted benzene.

In the present process, the previously isolated alkylbenzoylbenzoic acid can be dissolved in an inert solvent to form a solution of, say 5 to 30% concentration, or the solvent solution of alkylbenzoylbenzoic acid as prepared can be employed as a starting material. The solution is best added to oleum having a level of about 5 to 10% sulfur trioxide, allowing the reaction temperature to go as high as about 90° C. The mixture is then heated at 85° to 95° C to complete the ring closure.

Usually, about 3 to 5 hours heating is employed. After the ring closure is complete, water is added to dilute the sulfuric acid, forming two layers, one comprising the alkylanthraquinone product in solvent solution and the other comprising an aqueous solution of sulfuric acid. The solvent solution can be separated by decantation and then washed with warm water to void crystallization of the product and to promote easy separation of the aqueous wash layers. If desired, the alkylanthraquinone can be isolated by steam distilling the solvent from it, leaving a crude alkylanthraquinone which can be purified by distillation under reduced pressure. Alternatively, the mixture of alkylanthraquinone and solvent can be fractionally distilled directly to produce a purified product.

In the ring closure reactions of the prior art employing oleum, there is a tendency for undesirable by-product formation to occur as the alkyl group increases in molecular weight. By-product formation is caused by the sulfonating reaction that competes with the ring closure reaction, and results in lower yields of the desired alkylanthraquinone.

The improved process of this invention minimizes the above-described difficulties in several ways. Addition of a solution avoids local overconcentration of alkylbenzoylbenzoic acid. The solution readily disperses and mixes uniformly in the oleum, avoiding both excessive sulfonation and decomposition due to the action of the oleum. At the same time, the solution can be added rapidly, the heat of reaction carrying the temperature quickly to about 90° C, which temperature reduces processing time and appears to be optimum for the ring closure reaction. In this manner, it appears that the ring closure reaction is favored over the sulfonation reaction, and yields of 80 to 95% of theoretical can be obtained.

The addition of the solvent solution to the oleum is best done rapidly, as short a time as 15 minutes having been successfully employed. Little impairment of yield has been observed when times up to 5 hours were employed for the addition. Longer times may or may not lower yield, but heating for longer times does defeat the economic purpose of the process. Good agitation and efficient heat removal are necessary. There is considerable heat of reaction, and low temperature at the start of the addition has been found most practical for operation in plant scale batch equipment.

The process of the instant invention is characterized by providing good yields at high volume production levels within convenient processing times and at moderate reaction temperatures. Uses for the products of this process are known. For example, methylanthraquinone and ethylanthraquinone are employed in dye manufacture. Ethylanthraquinone and butyl and amylanthraquinones are used as oxygen carriers in the manufacture of hydrogen peroxide. Amylanthraquinone is better suited than ethylanthraquinone for this use because of its greater solubility in the solvents employed in the hydrogen peroxide process.

PREPARATION OF THE STARTING REACTANT

Following is a typical preparation of t-amylbenzoylbenzoic acid reactant.

To a suitable reactor, there was added 103.2 parts of trichlorobenzene, 12.38 parts of phthalic anhydride and 12.65 parts of crude t-amylbenzene (10.69 parts of 100%). The charge was cooled to 18° C and, with agitation and cooling, 21.0 parts of powdered aluminum chloride was added in portions of 1 part each to maintain the temperature at 20° to 25° C. After all of the aluminum chloride had been added, the charge was held at 20° to 25° C for 9 hours to complete the reaction. The charge was then dropped into 135 parts of 3% hydrochloric acid and held for severa hours at 70° C to decompose the aluminum chloride product complex, and the trichlorobenzene product solution isolated by decantation. The product solution was washed at 70° C with five 70 part water washes, separating each wash by decantation. Finally, the solution of t-amylbenzoylbenzoic acid in trichlorobenzene was dehydrated by heating under reduced pressure at 65° to 95° C until the solution contained less than 0.5% water as analyzed by the Karl Fischer method.

EXAMPLE 1

A solution was prepared of 100 grams of 85% purity amylbenzoylbenzoic in 600 grams of trichlorobenzene at 57° C. The solution was added rapidly to 500 grams of 5% oleum, maintaining temperature at 15° to 20° C. The temperature was then raised over a one-hour period to 90° C, and the charge was held at about 90° C for about 4 hours. The charge was then drowned in 1500 grams of ice water, heated to 60° C and then allowed to settle without stirring for ½ hour. The organic layer was washed 3 times with 1500-gram portions of water at 60° C, then washed finally with 1500 grams of water containing 5 grams of sodium carbonate. After separating the organic solution by decantation, it was distilled through a Vigreaux column under vacuum. There was obtained 560 grams of tri-chlorobenzene and 82 grams of amylanthraquinone-containing product having a purity of 95.7%, representing a yield of 98.3% of theoretical.

EXAMPLES 2 AND 3

To 400 parts of 10.5% oleum there was added a solution of 100 parts of tertiary butylbenzoylbenzoic acid in 600 parts of commercial trichlorobenzene. The solution was added gradually over a 30 minute period to the well-stirred oleum held at 80° to 90° C. After the addition was complete, the reaction mixture was stirred at 90° C for 4 hours, then poured into 2000 parts of cold water. The aqueous and organic layers were allowed to separate, and the aqueous layer was removed by decantation. After washing the organic layer twice with 800 part portions of water, the residual acidity was neutralized by stirring the organic layer with another 800 parts of water, sufficient 30% aqueous sodium hydroxide solution being added to achieve a pH above 7.0. A final 800 part water wash was applied, and the product was fractionally distilled. From 562 parts of crude product there was obtained 480 parts of trichlorobenzene, 80 parts of tertiary butylanthraquinone-containing product and 6 parts of residual high-boiling tar. The product was 98.4 % tertiary butylanthraquinone. The yield was 86% of theory.

In a parallel preparation, run in the same manner except that only 400 parts of trichlorobenzene was employed instead of 600 parts, the purity of the product was 98.2% tertiary butylanthraquinone, with the yield being 83% of theory. Purity of the products in both instances was determined by vapor phase chromatograph analysis.

EXAMPLE 4

The strength of the oleum employed was 8.8%, and the concentration of amylbenzoylbenzoic acid in trichlorobenzene solution was 20%. To 447 grams of the oleum mixture there was added 406 grams of 20 % solution of amylbenzoylbenzoic acid in trichlorobenzene. The addition was made gradually over a 10 minute period while holding the temperature in the reaction mass below 20° C. The temperature was raised to 90° C and held at that level for 4 hours. Then, the reaction mixture was drowned in 2000 ml of cold water. The temperature was next adjusted to just below 70° C and the organic layer was separated by decantation. It was washed twice with 800 ml portions of water, then with 800 ml of water containing 5 grams of 30% sodium hydroxide and finally with another 800 ml of water. The washed trichlorobenzene-amylanthraquinone solution weighed 345 g. Vacuum distillation at 3 mm absolute pressure indicated 18.5% organic solids that were analyzed by vapor phase chromatography and found to be 94.2% amylanthraquinone. The yield of 100% of amylanthraquinone was 92.8% of theory.

EXAMPLE 5

To 650 parts of 5.5% oleum there was added a solution of 65 parts of 2-(4-tert-amylbenzoyl)benzoic acid in 435 parts of trichlorobenzene. At the beginning of the addition, the oleum was at 25° to 30° C. The trichlorobenzene solution was added over a one-hour period in successive portions, by weight, of 10, 20, 30 and 50%, at 15 minute intervals. The temperature was allowed to raise to 90 ° to 95° C at the end of the addition. The charge was held at 87° to 93° C for 4 hours, then dropped into 2000 parts of water (not above 35° C) allowing the temperature to rise no higher than 90° C. The aqueous and organic layers were separated at at temperature of 75° to 80° C. The charge was washed successively with water, sodium hydroxide solution and water as in Examples 2 and 3. The trichlorobenzene was then removed by steam distillation. Wkhen the trichlorobenzene was completely removed, the temperature of the charge was gradually raised to 127° C to 132° C to remove the residual water and melt the crude 2-amylanthraquinone product, which was then collected and weighed and analyzed. There was obtained 58.3 parts of crude product having a purity of 90%. The yield was 86% of theoretical. About 70% of the trichlorobenzene employed was recovered in the distilliation step.

The embodiments of the invention in which an exclusive property or privilege is claimed are defined as follows:

1. In a process for preparing alkylanthraquinone comprising heating alkylbenzoylbenzoic acid in the presence of oleum, the improvement comprising
   i. forming a solution of one part of alkylbenzoylbenzoic acid in at least five parts by weight of trichlorobenzene, said alkyl group having 4 or 5 carbon atoms, and
   ii. reacting the solution of (i) with at least four parts of oleum per part of alkylbenzoylbenzoic acid at a temperature from 85° to 95° C, thereby forming alkylanthraquinone in solution, with said alkyl group having 4 or 5 carbon atoms.

2. A process according to claim 1 wherein the alkylbenzoylbenzoic acid is tertiary butylbenzoylbenzoic acid.

3. A process according to claim 1 wherein the alkylbenzoylbenzoic acid is tertiary pentylbenzoylbenzoic acid.

* * * * *